(12) United States Patent
Jumawid et al.

(10) Patent No.: US 8,357,502 B2
(45) Date of Patent: Jan. 22, 2013

(54) METHOD FOR MEASURING LOW DENSITY LIPOPROTEIN CHOLESTEROL

(75) Inventors: Mariejoy Jumawid, Kanagawa (JP); Hiroko Inomata, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 330 days.

(21) Appl. No.: 12/730,437

(22) Filed: Mar. 24, 2010

(65) Prior Publication Data

US 2010/0248276 A1     Sep. 30, 2010

(30) Foreign Application Priority Data

Mar. 25, 2009 (JP) .................... 2009-073999

(51) Int. Cl.
*C12Q 1/60* (2006.01)
(52) U.S. Cl. ............................ 435/11; 436/71
(58) Field of Classification Search ............. 435/11; 436/71
See application file for complete search history.

(56) References Cited

U.S. PATENT DOCUMENTS

| 4,424,191 A | 1/1984 | Jakubowicz |
| 6,794,157 B1 | 9/2004 | Sugiuchi |

FOREIGN PATENT DOCUMENTS

| EP | 0 244 825 | 11/1987 |
| EP | 1 114 870 | 7/2001 |
| EP | 2 065 708 | 6/2009 |
| EP | 2065708 A1 * | 6/2009 |
| JP | 55-164356 | 12/1980 |
| JP | 56-142454 | 10/1981 |
| JP | 57-066359 | 4/1982 |
| JP | 58-032350 | 3/1983 |
| JP | 58-501144 | 7/1983 |
| JP | 58-161867 | 9/1983 |
| JP | 57-063452 | 4/1985 |
| JP | 60-125543 | 7/1985 |
| JP | 60-220862 | 11/1985 |
| JP | 60-222769 | 11/1985 |
| JP | 60-222770 | 11/1985 |
| JP | 61-294367 | 12/1986 |
| JP | 62-182652 | 8/1987 |
| JP | 63-109799 | 5/1988 |
| JP | 63-219397 | 9/1988 |
| JP | 2009-125049 | 6/2009 |
| WO | 83-00391 | 2/1983 |
| WO | 00/17388 | 3/2000 |

OTHER PUBLICATIONS

European Patent Office issued an European Search Report dated Jul. 7, 2010, Application No. 10157508.2.

* cited by examiner

*Primary Examiner* — Ralph Gitomer
(74) *Attorney, Agent, or Firm* — Young & Thompson

(57) ABSTRACT

It is an object of the present invention to provide a method for measuring low density lipoprotein cholesterol (LDL-C) in a body fluid, which is able to selectively measure low density lipoprotein cholesterol in a body fluid without using a low density lipoprotein cholesterol-selective surfactant having a risk of generating endocrine-disrupting chemicals. The present invention provides a method for measuring low density lipoprotein cholesterol (LDL-C) in a body fluid, which comprises measuring low density lipoprotein cholesterol (LDL-C) by using (a) cholesterol esterase and (b) cholesterol oxidase or cholesterol dehydrogenase, in the presence of a polyoxyethylene-polyoxypropylene copolymer and a polyglyceryl ether.

13 Claims, 3 Drawing Sheets

METHOD FOR MEASURING LOW DENSITY LIPOPROTEIN CHOLESTEROL

TECHNICAL FIELD

The present invention relates to a method for measuring low density lipoprotein cholesterol (LDL-C) in a specimen.

BACKGROUND ART

Lipids present in blood are incorporated into the structure of lipoprotein, except for free fatty acid bound with albumin, and they are present in the form of a chylomicron (CHM), a very low density lipoprotein (VLDL), a low density lipoprotein (LDL), a high density lipoprotein (HDL), and the like. Cholesterol is particularly distributed in VLDL, LDL, and HDL. It has been known that a high level of LDL which acts to transport cholesterol, promotes arteriosclerosis. It has been known that the measurement of the level of low density lipoprotein cholesterol (LDL-C) in blood is useful for an indicator for the development and progression of arteriosclerosis.

International Publication WO00/17388 describes a method for quantifying LDL cholesterol in a biological sample, which is characterized in that, in (a) a biological sample, (b) cholesterol esterase and cholesterol oxidase or cholesterol dehydrogenase (herein referred to as CH enzymes), and (c) a low density lipoprotein (hereinafter referred to as LDL), a reaction of cholesterol is carried out in the presence of a reagent for allowing the CH enzymes described in (b) above to act on only cholesterol in the low density lipoprotein (herein referred to as LDL cholesterol), and the generated hydrogen peroxide or reduced coenzyme is then measured, so as to quantify the concentration of the LDL cholesterol. In International Publication WO00/17388, a polyoxyethylene-polyoxypropylene copolymer and a polyoxyethylene derivative are used as LDL selective reagents. However, even by quantifying LDL-C according to the method described in International Publication WO00/17388, there may be a case in which the selectivity for LDL-C is insufficient. In addition, polyoxyethylene alkyl aryl ether, which is used as a polyoxyethylene derivative in International Publication WO00/17388, unfavorably contains a compound that may cause environmental hormone risk.

JP Patent Publication (Kokai) No. 63-109799 (1988) A describes a dry analytical element, which comprises at least one water-permeable layer and a porous liquid spreading layer in a state in which the layers may be allowed to come into contact with a liquid, wherein the dry analytical element further comprises an enzyme having cholesterol ester hydrolyzing activity in the above-described spreading layer and alkyl phenoxy polyglycidol in the above-described spreading layer or the above-described at least one water-permeable layer. The polyglycidol described in JP Patent Publication (Kokai) No. 63-109799 (1988) is used to improve coating property. The dry analytical element described in JP Patent Publication (Kokai) No. 63-109799 (1988) does not have the selectivity for low density lipoprotein cholesterol (LDL-C).

DISCLOSURE OF THE INVENTION

It is an object of the present invention to provide a method for measuring low density lipoprotein cholesterol (LDL-C) in a body fluid, which is able to selectively measure low density lipoprotein cholesterol in a body fluid without using a low density lipoprotein cholesterol-selective surfactant having a risk of generating endocrine-disrupting chemicals.

As a result of intensive studies directed towards achieving the aforementioned object, the present inventors have found that low density lipoprotein cholesterol (LDL-C) can be selectively measured by using (a) cholesterol esterase and (b) cholesterol oxidase or cholesterol dehydrogenase in the presence of a polyoxyethylene-polyoxypropylene copolymer and a polyglyceryl ether, and that this measurement method is excellent in tetras of multi-specimen correlation. The present invention has been completed based on these findings.

The present invention provides a method for measuring low density lipoprotein cholesterol (LDL-C) in a body fluid, which comprises measuring low density lipoprotein cholesterol (LDL-C) by using (a) cholesterol esterase and (b) cholesterol oxidase or cholesterol dehydrogenase, in the presence of a polyoxyethylene-polyoxypropylene copolymer and a polyglyceryl ether.

Preferably, the polyglyceryl ether is an aliphatic hydrocarbon polyglyceryl ether or polycyclic polyglyceryl ether.

Preferably, the polycyclic polyglyceryl ether is a compound represented by the following formula (1):

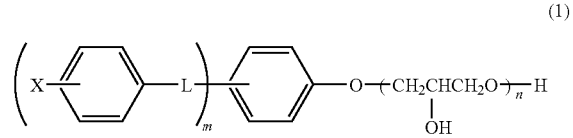

(1)

wherein X represents a hydrogen atom, a C1-C18 alkyl group, or a halogen atom, wherein the alkyl group may be either a linear or branched alkyl group; L represents a C1-C5 alkylene group; m represents an integer of 1 to 5; and n represents an integer of 3 to 20.

Preferably, low density lipoprotein cholesterol is measured by allowing peroxidase and a chromogen to act on hydrogen peroxide generated from the low density lipoprotein cholesterol by cholesterol esterase and cholesterol oxidase, so as to carry out a color development reaction.

The present invention provides a reagent for measuring low density lipoprotein cholesterol (LDL-C), which comprises (a) cholesterol esterase, (b) cholesterol oxidase or cholesterol dehydrogenase, (c) a polyoxyethylene-polyoxypropylene copolymer, and (d) a polyglyceryl ether.

Preferably, the polyglyceryl ether is an aliphatic hydrocarbon polyglyceryl ether or polycyclic polyglyceryl ether.

Preferably, the polycyclic polyglyceryl ether is a compound represented by the following formula (1):

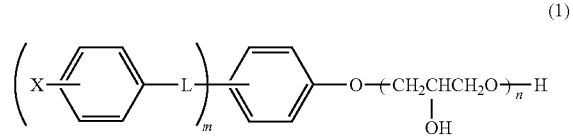

(1)

wherein X represents a hydrogen atom, a C1-C18 alkyl group, or a halogen atom, wherein the alkyl group may be either a linear or branched alkyl group; L represents a C1-C5 alkylene group; m represents an integer of 1 to 5; and n represents an integer of 3 to 20.

The present invention provides a kit for measuring low density lipoprotein cholesterol (LDL-C), which comprises (a) cholesterol esterase, (b) cholesterol oxidase, (c) peroxidase, (d) a chromogen, (e) a polyoxyethylene-polyoxypropylene copolymer, and (f) a polyglyceryl ether.

The present invention provides a dry analytical element for measuring low density lipoprotein cholesterol (LDL-C), which comprises (a) cholesterol esterase, (b) cholesterol oxidase, (c) peroxidase, (d) a chromogen, (e) a polyoxyethylene-polyoxypropylene copolymer, and (f) a polyglyceryl ether.

According to the present invention, low density lipoprotein cholesterol can be selectively measured. Since a surfactant having no risk of generating endocrine-disrupting chemicals is used in the present invention, it is safe to the environment. Moreover, the method for measuring low density lipoprotein cholesterol according to the present invention has excellent multi-specimen correlation.

EMBODIMENT FOR CARRYING OUT THE INVENTION

Figure 1:
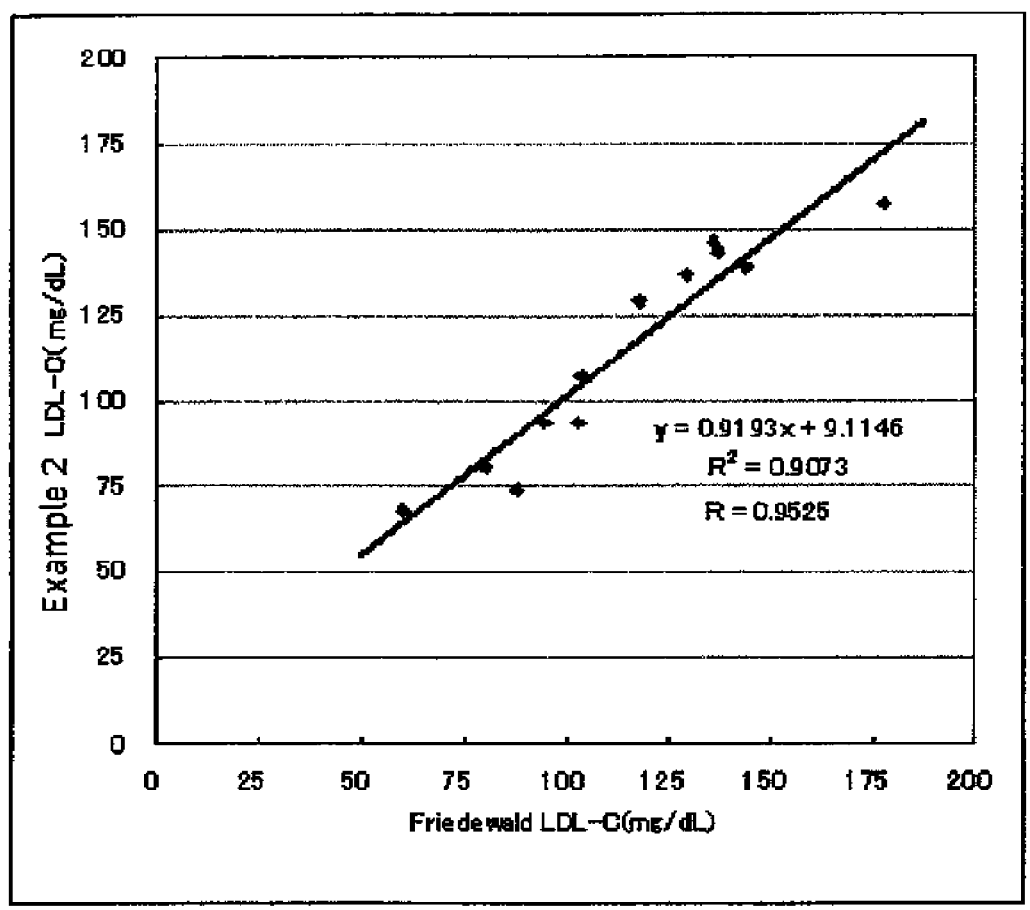
FIG. 1 shows a multi-specimen correlation in the method of the present invention.

Hereinafter, the embodiments of the present invention will be described in detail.

The method of the present invention is a method for measuring low density lipoprotein cholesterol (LDL-C) in a body fluid, which comprises measuring low density lipoprotein cholesterol (LDL-C), using (a) cholesterol esterase and (b) cholesterol oxidase or cholesterol dehydrogenase, in the presence of a polyoxyethylene-polyoxypropylene copolymer and a polyglyceryl ether.

As a body fluid, blood, urine, or the like can be used. Blood or urine may be directly used as a body fluid sample. Otherwise, blood or urine, which had been pre-treated as appropriate, may also be used.

The polyoxyethylene-polyoxypropylene copolymer used in the present invention may be either a random copolymer or block copolymer composed of polyoxyetylene and polypropylene. An example is a compound represented by the formula: HO—$(C_2H_4O)_a$—$(C_3H_6O)_b$—$(C_2H_4O)_c$—H [wherein a, b, and c identically or differently represent an integer of 1 to 200]. Examples of the compound represented by the above-mentioned formula include commercially available products such as Pluronic L-121, Pluronic L-122, Pluronic L-101, Pluronic P-103, and Pluronic F-108 (all of which are manufactured by ADEKA CORPORATION). In addition, the molecular weight of a polypropylene glycol group contained in the compound represented by the above-mentioned compound is preferably 2,050 or greater, more preferably 2,750 or greater, and particularly preferably 3,250 or greater. The HLB of the polyoxyethylene-polyoxypropylene copolymer is preferably 1 to 6. The concentration of the polyoxyethylene-polyoxypropylene copolymer used is not particularly limited. It is preferably 0.001% to 20%, and more preferably 0.01% to 10%.

The structure of the polyglyceryl ether used in the present invention is not particularly limited. It is preferably an aliphatic hydrocarbon polyglyceryl ether (for example, alkyl polyglyceryl ether) or polycyclic polyglyceryl ether.

The term "polycyclic polyglyceryl ether" is used in the present specification to mean a compound having a partial structure in which two or more rings are present at one terminus of a polyglycidol chain. Such compound preferably has aryl group that binds to one terminus of the polyglycidol chain, wherein the aryl group has one or two or more aryl groups binding thereto via a linker(s), as necessary. Such compound more preferably has aryl group that binds to one terminus of the polyglycidol chain, wherein the aryl group has a structure in which one or two or more aryl groups binding thereto via a linker(s). In the aforementioned polycyclic polyglycidol compound, the aryl ring is preferably a benzene ring. As a linker, a linear or branched alkylene group or the like may be used. The alkylene group may have a substituent, as necessary, and it may comprise a heteroatom such as a nitrogen atom, an oxygen atom, or a sulfur atom, in the main chain. An aryl group(s) binding to the aryl ring via a linker(s) as necessary are preferably a phenyl group(s). It is preferable that two or more phenyl groups bind to the aryl ring via linkers. Such phenyl group may have one or two or more substituents.

As a polycyclic polyglyceryl ether, a compound represented by the following formula (1) is preferable.

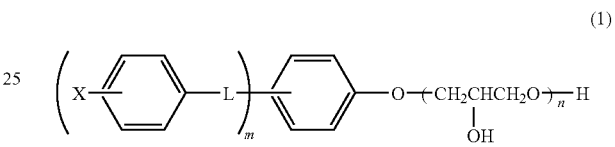

(1)

wherein X represents a hydrogen atom, a C1-C18 alkyl group, or a halogen atom, wherein the alkyl group may be either a linear or branched alkyl group; L represents a C1-C5 alkylene group; m represents an integer of 1 to 5; and n represents an integer of 3 to 20.

The C1-C5 alkylene group represented by L may be either a linear or branched group. As a methylene unit that constitutes L, a methylene unit represented by —$C(R^1)(R^2)$— (wherein each of $R^1$ and $R^2$ independently represents a hydrogen atom or a $C_1$-$C_4$ alkyl group) is preferable, and an alkylene group containing the above-described 1 to 5 methylene units is preferable. It is preferable that, in the above-described methylene unit, $R^1$ be a hydrogen atom and $R^2$ be a hydrogen atom or a methyl group. When such alkylene group contains the above-described two or more methylene units, such methylene units may be identical to or different from one another. More specific examples include a methylene group, a methyl methylene group, an ethylene group, a methyl ethylene group, a propylene group, and a butylene group. The alkylene group represented by L preferably comprises a single methylene unit. L is more preferably a group represented by —$C(R^1)(R^2)$—. In this case, it is more preferable that $R^1$ be a hydrogen atom and $R^2$ be a hydrogen atom or a methyl group.

X represents a hydrogen atom, a C1-C18 alkyl group, or a halogen atom. C1-C18 alkyl group may be any one of a linear group, a branched group, a cyclic group, and a combination thereof. Examples of alkyl group include a methyl group, an ethyl group, an n-propyl group, an isopropyl group, an n-butyl group, a tert-butyl group, a 2-ethylhexyl group, an octyl group, a nonyl group, and a decyl group. As a halogen atom, a fluorine atom, a chlorine atom, or a bromine atom may be used. The position and number of the group represented by X are not particularly limited. When the compound has two or more substituents X, such substituents may be identical to or different from one another.

The letter m represents an integer of 1 to 5. When m is an integer of 2 or greater, the groups may be identical to or different from one another. The letter m represents an integer of, preferably 1 to 3, more preferably 2 or 3, and particularly preferably 3.

The letter n represents an integer of 3 to 20. It is an integer of, preferably 5 to 18, and more preferably 8 to 16.

There may be a case in which the polycyclic polyglyceryl ether represented by the above formula (1) has one or two or more asymmetric carbon atoms, and in which a stereoisomer (an optical isomer or a diastereoisomer) is present due to such asymmetric carbon atom(s). All of any given stereoisomer that has a pure form, any given mixture of such stereoisomers, and a racemic form, and the like can be used in the method of the present invention. Moreover, there may also be a case in which the polycyclic polyglyceryl ether represented by the above formula (1) is present in the form of any given hydrate or solvate. These substances can also be used in the method of the present invention.

Specific examples of the polycyclic polyglyceryl ether represented by the above formula (1) are given below. In all of them, the binding position of a substituted benzyl group to a benzene ring is not particularly limited.

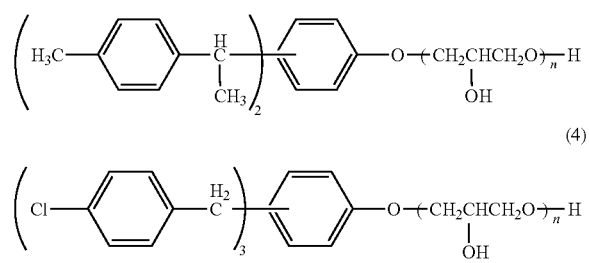

Particularly preferred compound (5) to compound (10) are shown below (wherein the binding position of a substituted benzyl group to a benzene ring is not particularly limited).

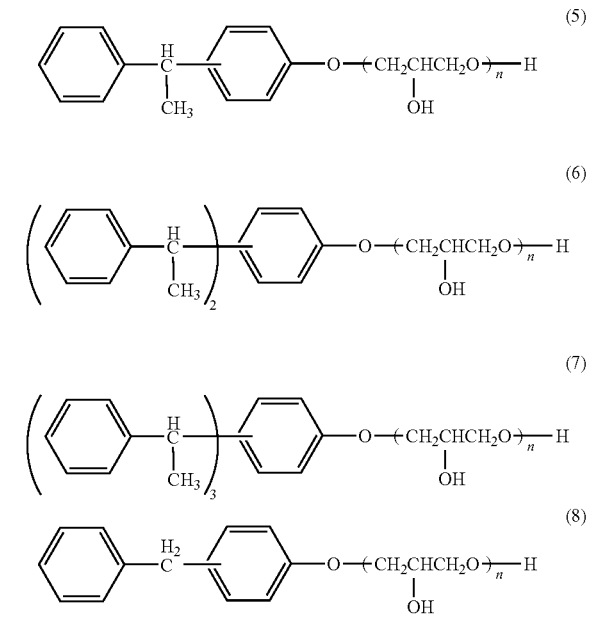

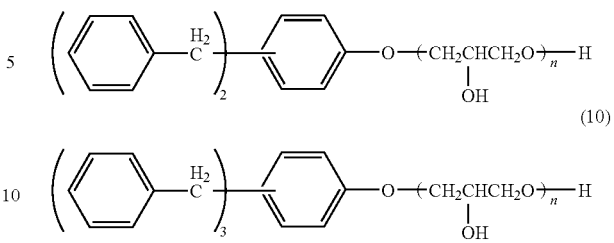

The polycyclic polyglyceryl ether represented by the formula (1) can be produced, for example, by adding glycidol to a phenol compound represented by the following formula (11) in the presence of a catalyst:

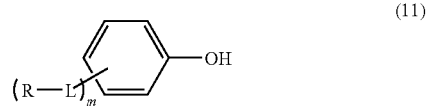

(wherein R represents an aryl group (wherein the aryl group may have one or two or more substituents selected from the group consisting of a $C_1$-$C_{18}$ alkyl group and a halogen atom); and L and m have the same above definitions.) In this reaction, it is possible to change the length of a glycidol chain by changing the ratio between the phenol compound used as a raw material compound and the glycidol.

As a catalyst, an alkali catalyst is used. Examples of alkali catalyst include the hydroxides of alkaline metal and alkaline-earth metal, such as lithium hydroxide, sodium hydroxide, potassium hydroxide, cesium hydroxide, magnesium hydroxide, calcium hydroxide, and barium hydroxide. Of these, sodium hydroxide, potassium hydroxide, and cesium hydroxide are preferable, and potassium hydroxide is particularly preferable. With regard to the amount of such catalyst used, the catalyst is used at a percentage of 0.0001% to 1%, preferably 0.001% to 0.8%, and particularly preferably 0.005% to 0.5%, with respect to the raw material compound. The aforementioned reaction can be generally carried out in the absence of solvent. The reaction temperature is from room temperature to 200° C., preferably from 50° C. to 200° C., and more preferably from 100° C. to 180° C. The reaction time depends on the reaction temperature. It is 1 to 150 hours, more preferably 2 to 24 hours, and particularly preferably 2 to 10 hours.

After completion of the reaction, the temperature of the reaction solution is returned to room temperature, and the reaction solution is then neutralized with an acid, followed by the treatments according to an ordinary method, so as to isolate a product of interest. Examples of acid include: mineral acids such as hydrochloric acid, sulfuric acid, nitric acid, hydrobromic acid and phosphoric acid; and organic acids such as methanesulfonic acid, ethanesulfonic acid, acetic acid and p-toluenesulfonic acid. Preferably, hydrochloric acid, sulfuric acid, phosphoric acid, methanesulfonic acid, and acetic acid can be used. The use of hydrochloric acid, phosphoric acid, methanesulfonic acid, and acetic acid is particularly preferable. After completion of the neutralization, when a product of interest is insoluble in water, such product of interest can be isolated by filtration. When the product of interest has high viscosity, water may be added, and the product of interest may be obtained in the state of an aqueous solution. There may be a case in which the polyglycidol compound represented by the aforementioned formula (1) is produced in the form of a mixture of compounds having different n numbers. Such mixture can be used as a surfactant in the method of the present invention.

It is to be noted that the aforementioned polycyclic polyglyceryl ether used in the present invention is described in Japanese Patent Application No. 2007-306716, and that the disclosures thereof are incorporated herein by reference in their entirety.

Examples of enzymes used in the method of the present invention include cholesterol esterase, and cholesterol oxidase or cholesterol dehydrogenase. As cholesterol esterase, lipase can also be used. The types of microorganisms, from which such enzymes are derived, are not particularly limited. For example, with regard to cholesterol esterase, *Schizophyllum commune*-derived or *Pseudomonas* sp.-derived esterase, or esterase derived from other types of microorganisms can be used. With regard to cholesterol oxidase, *Pseudomonas* sp.-derived, *Streptomyces* sp.-derived, or other types of microorganisms-derived oxidase can be used. The enzyme used in the present invention may be either an enzyme derived from such microorganisms, or a recombinant enzyme produced by a publicly known method.

An example of cholesterol esterase derived from *Schizophyllum commune* is COE-302 manufactured by Toyobo Co., Ltd. Examples of cholesterol esterase derived from *Pseudomonas* sp. include COE-311, LPL-312 and LPL-314 manufactured by Toyobo Co., Ltd., and CEN manufactured by Asahi Kasei Corporation. Examples of cholesterol oxidase derived from *Pseudomonas* sp. include CHO-PEL and CHO-PEWL manufactured by Kikkoman Corporation.

In the method of the present invention, in addition to the aforementioned reagents, reagents for detecting cholesterol, such as an enzyme reagent, a chromogen, and a pH buffer, which are publicly known, can also be used.

More specifically, peroxidase can be used as an enzyme. As chromogen, 4-aminoantipyrine (4-AA), a phenolic or aniline Trinder's reagent that develops color as a result of hydrogen-donating coupling, a leuco dye, or the like can be used. As Trinder's reagent, an aniline reagent can be preferably used. Examples of aniline Trinder's reagent include
N-ethyl-N-sulfopropyl-3-methoxyaniline (ADPS),
N-ethyl-N-sulfopropylaniline (ALPS),
N-ethyl-N-sulfopropyl-3-methylaniline (TOPS),
N-ethyl-N-(2-hydroxy-3-sulfopropyl)-3-methoxyaniline (ADOS),
N-ethyl-N-(2-hydroxy-3-sulfopropyl)-3,5-dimethoxyaniline (DAOS),
N-(2-hydroxy-3-sulfopropyl)-3,5-dimethoxyaniline (HDAOS),
N-ethyl-N-(2-hydroxy-3-sulfopropyl)-3,5-dimethylaniline (MAOS), and
N-ethyl-N-(2-hydroxy-3-sulfopropyl)-3-methoxyaniline (TOOS) (manufactured by Dojindo Laboratories).

Examples of a pH buffer include carbonate, sulfate, phosphate, and a Good's pH buffer described in Biochemistry, 5, pp. 467-477, 1966. These pH buffers can be selected with reference to the descriptions of publications, such as *Tanpakushitsu Koso no Kiso Jikken Ho* (Basic Experimental Methods for Proteins and Enzymes), Takeichi Horio et al., Nankodo Co., Ltd., 1981, and Biochemistry, 5, pp. 467-477, 1966.

The pH of the aforementioned buffer can be determined depending on the optimal pH of enzyme used. The pH can be adjusted to preferably pH 5.0 to 8.0, and more preferably pH 6.0 to 7.0.

The measurement method of the present invention in a case in which a measurement system is a solution will be described below. However, the below-mentioned specific embodiment is not intended to limit the scope of the present invention. A reagent solution preferably has a composition consisting of (1) to (7) below
(1) Cholesterol esterase
(2) Cholesterol oxidase
(3) A polyoxyethylene-polyoxypropylene copolymer
(4) Polyglyceryl ether
(5) Peroxidase
(6) Chromogens (4-AA and a Trinder's reagent)
(7) pH buffer 1 to 1,000 µL of, and preferably 100 to 500 µL of a reagent solution prepared by mixing the above-described reagents to each have optimal concentrations is pre-incubated for 1 to 10 minutes, at a constant temperature from approximately 20° C. to approximately 45° C., and preferably from approximately 30° C. to approximately 40° C. Thereafter, 0.5 to 50 µL of, and preferably 1 to 20 µL of a solution sample is added to the above-described reagent solution. While incubating at a constant temperature, a change over time in wavelength due to the color development of the chromogens is measured. Using the previously prepared calibration curve, the amount of a test substance in a specimen can be obtained in accordance with the principle of colorimetry.

The necessary amounts of enzymes can be determined, as appropriate. For example, all of cholesterol esterase, cholesterol oxidase and peroxidase are used, preferably within the range between 0.2 and 500 U/mL, more preferably within the range between 0.2 and 100 U/mL, and further preferably within the range between 1 and 50 U/mL.

When the measurement system is a solution, only a polyoxyethylene-polyoxypropylene copolymer and a polyglyceryl ether may be used as surfactants. As necessary, one or two or more types of other surfactants may be used in combination with them. The concentration of surfactant is not particularly limited. For example, the surfactant can be used at a concentration of preferably 0.01% to 20%, and more preferably 0.1% to 15%.

The measurement method of the present invention using a dry analytical element, in which the measurement system is a dry reagent, will be described. The dry analytical element can be configured to have at least one adhesion layer and a porous spreading layer on a water-impermeable support.

The porous layer may be made of either a fibrous or non-fibrous material. Since such porous layer functions as a layer for spreading a liquid sample, it is preferably a layer having an action to measure liquid. The term "an action to measure liquid" is used herein to mean an action to extend to a lateral orientation to the layer, a liquid sample spotted onto the surface of the layer, at a rate of an almost constant amount per unit area, substantially without uneven distribution of ingredients contained therein. In order to control the spreading area, the spreading rate, and the like, the hydrophilic polymer or surfactant described in JP Patent Publication (Kokai) Nos. 60-222770 A (1985), 63-219397 A (1988), and 62-182652 A (1987) can be mixed into the spreading layer. It can also be possible to mix a polycyclic polyglycidol compound as a surfactant into the spreading layer.

A fibrous porous layer is preferably made of polyester fibers, including those described in JP Patent Publication Nos. 55-164356 A (1980), 57-66359 A (1982) and 60-222769 A (1985), as typical examples. A non-fibrous porous layer is preferably made of an organic polymer such as polysulfonic acid.

An adhesion layer is a layer having a function of adhering the above-described water-impermeable support to the above-described porous layer. Examples of such adhesion layer that can be used herein include hydrophilic polymers such as gelatin and the derivatives thereof (e.g. phthalate gelatin), cellulose derivatives (e.g. hydroxypropyl cellulose), agarose, acrylamide polymers, methacrylamide polymers, and copolymers of acrylamide or methacrylamide with various types of vinyl monomers.

An aqueous solution containing a hydrophilic polymer is uniformly coated by a publicly known method. Known methods for coating such aqueous solution can be used. In order to coat an aqueous solution containing a hydrophilic polymer, a method may be appropriately selected from among dip coating, extruding coating, doctor coating, hopper coating, curtain coating, and the like, and it may be then used.

It may also be possible to coat the porous layer onto the adhesion layer. However, it is preferable to laminate a cloth or a porous membrane that has previously been supplied as a fabric on the adhesion layer. As a lamination method, as described in JP Patent Publication (Kokai) No. 55-164356 A (1980), the surface of an adhesion layer containing a hydrophilic polymer is uniformly moistened with water, and a cloth or a porous membrane is then placed on the adhesion layer. Thereafter, pressure is lightly and uniformly added thereon, so that the cloth or porous membrane can adhere to the adhesion layer. The thickness of such adhesion layer is preferably 0.5 to 50 µM, and more preferably 1 to 20 µm.

Preferred materials for a light-permeable support include cellulose ethers such as polyethylene terephthalate, polystyrene, and cellulose triacetate. In order to strongly adhere a water-absorbing layer as a hydrophilic layer, a detection layer, a substantially non-porous reagent layer, and the like to a support, it may be generally possible to establish an undercoating layer on the support, or to perform a hydrophilic treatment thereon. The thickness of the support is not particularly limited. It is preferably 10 to 1,000 µm, and more preferably 300 to 800 µm. In the case of a light-permeable support, the final detection may be carried out either on the support side or the porous layer side. On the other hand, in the case of a light-impermeable support, the final detection is carried out on the porous layer side.

As necessary, a stabilizer, a pH buffer, a crosslinker (a hardener or a curing agent), a surfactant, a polymer, and the like may be used. These agents may be contained in the adhesion layer or the porous layer.

The reagent compositions used for the measurement of cholesterol and the reagent compositions that bring on an optical change, which are used for a dry analytical element, will be described.

The reagent compositions may be contained in a first porous layer. However, such reagent compositions may also be contained in both an adhesion layer and a porous layer. Otherwise, all of or a majority of reagent compositions may be contained in any one of such layers, or such reagent compositions may previously be added to any layer other than the adhesion layer and the porous layer.

In a dry analytical element used for LDL-C detection, all enzymes, namely, cholesterol esterase, and cholesterol oxidase or cholesterol dehydrogenase, may be each used in an amount of preferably approximately 0.1 to 30 kU per $m^2$, and more preferably approximately 0.5 to 15 kU per $m^2$.

A surfactant may be used in an amount of approximately 0.2 to 30 g per $m^2$, and more preferably approximately 1 to 20 g per $m^2$.

The type of peroxidase is not particularly limited. Horseradish peroxidase is preferable. Peroxidase may be used in an amount of preferably approximately 1 to 200 $kU/m^2$, and more preferably approximately 10 to 100 $kU/m^2$.

With regard to the above-mentioned chromogen, the combination of the above reagent that couples with 4-aminoantipyrine (4-AA) to develop color is preferable. Particularly preferably, N-ethyl-N-(2-hydroxy-3-sulfopropyl)-3,5-dimethoxyaniline sodium salts (DAOS) can be used. The amount of chromogen used is not particularly limited. For example, 4-AA and a hydrogen-donating coupling agent may be each used in an amount of preferably approximately 0.1 to 10 $g/m^2$, and more preferably approximately 0.1 to 5 $g/m^2$.

As other reagent compositions, the dry analytical element used for the detection of LDL-C may further comprise one or two or more types of additives such as a stabilizer, a pH buffer, a crosslinker (a hardener or a curing agent), a surfactant and a polymer, as necessary. These additives may be contained in the adhesion layer and/or porous layer of the dry analytical element.

The pH of a buffer may be determined depending on the optimal pH of enzyme used. The pH can be adjusted to preferably pH 5.0 to 8.0, and more preferably pH 6.0 to 7.0.

The dry analytical element of the present invention preferably comprises a layer which contains chromogen and peroxidase, and a layer which contains cholesterol esterase, cholesterol oxidase, polyoxyethylene-polyoxypropylene copolymer and polyglyceryl ether.

The dry analytical element can be cut into, for example, small pieces such as a square of approximately 5 mm to approximately 30 mm on a side or a circle having almost the same size, and it can be then placed in a slide frame described in JP Patent Publication (Kokoku) No. 57-283331 B (1982), JP Utility Model Publication (Kokai) No. 56-142454 U (1981), JP Patent Publication (Kokai) No. 57-63452 A (1982), JP Utility Model Publication (Kokai) No. 58-32350 U (1983), JP Patent Publication (Kohyo) No. 58-501144 A (1983), etc., so that it can be used as a chemical analysis slide. This embodiment is preferable from the viewpoint of production, packaging, transport, storage, measurement procedures, and so on. Depending on the purpose of usage, the dry analytical element may be placed in a long tape form in a cassette or magazine for use. Alternatively, the small piece thereof may be placed in a container with an opening for use, or may be attached to or placed in an opening card for use. Otherwise, the small cut piece may further be used directly.

Upon application of the dry analytical element, an aqueous liquid sample solution (for example, a body fluid sample such as blood or urine) may be spotted in a range of; for example, approximately 2 µL to approximately 30 µL, and preferably 4 µL to 15 µL, onto the porous liquid sample spreading layer in the dry analytical element. Thereafter, the dry analytical element, on which the sample solution has been spotted, may be incubated at a constant temperature ranging from approximately 20° C. to approximately 45° C., preferably from approximately 30° C. to approximately 40° C., for 1 to 10 minutes. Color development or discoloration within the dry analytical element may be reflex-measured from the light-permeable support side. A calibration curve prepared in advance may be used to determine the amount of the test substance in the specimen according to the principle of colorimetry.

The measurement procedures can be carried out extremely easily using the chemical analyzers described in JP Patent Publication (Kokai) Nos. 60-125543 A (1985), 60-220862 A (1985), 61-294367 A (1986), and 58-161867 A (1983), etc. thereby performing quantitative analysis with high precision. Depending on purposes and necessary precision, the degree of color development may be assessed by visual observation to perform semiquantitative measurement.

The dry analytical element may be stored in a dry state until analysis. Accordingly, the reagents do not have to be prepared before use. Moreover, reagents in a dry state generally have high stability. Therefore, the method of the present invention is more convenient and rapid than a so-called solution method in which reagent solutions must be prepared before use. Moreover, the method of the present invention is also excellent as an examination method capable of rapid examination with high precision using a trace amount of liquid sample.

The present invention will be more specifically described in the following examples. However, these examples are not intended to limit the scope of the present invention.

EXAMPLES

Example 1

Evaluation of Selectivity for Low Density Lipoprotein (LDL)

Preparation of Samples 101 to 106 of the Present Inventions and Comparative Examples
Reagent 1

| | |
|---|---|
| MOPS (pH buffer, pH 7.0) | 50 mM |
| DAOS (manufactured by Dojindo Laboratories) | 1 mM |

(DAOS is a chromogen.)

Reagent 2

| | |
|---|---|
| MOPS (pH 7.0) | 50 mM |
| 4-aminoantipyrine | 2.5 mM |
| Pluronic L121 | 2.65% |
| Polyglyceryl dodecyl ether (surfactant 2) | 0.21% |
| Peroxidase (manufactured by Toyobo Co., Ltd.) | 20 U/ml |
| Cholesterol esterase (lipoprotein lipase, Toyobo) | 1 U/ml |
| Cholesterol oxidase (recombinant $E.\ coli$, Kikkoman) | 3 U/ml |

80 mg/dL HDL-C and 250 mg/dL LDL-C were used as a specimen. 480 μL of reagent 1 was mixed with 160 μL of reagent 2, and the mixture was then incubated at 37° C. for 5 minutes. Five minutes later, 13 μL of the specimen was added to the resultant, and they were then reacted at 37° C. for 5 minutes, so as to prepare sample 101.

The same above operations were carried out with the exception that the amount of Pluronic L121 and the type and amount of surfactant 2 in reagent 2 of the sample 101 were changed as shown in Table 1, so as to prepare samples 102 to 106.

The prepared samples were each measured using spectrophotometer, in terms of the absorbance at 600 nm 5 minutes later, and the results were summarized in Table 2. The term "$A_{HDL80}/A_{LDL250}$" is used herein to indicate an indicator with respect to the selectivity for LDL. The smaller the value, the higher the selectivity for LDL that can be obtained. Thus, it is found that the samples of the present invention all bring on high selectivity for LDL.

TABLE 1

| Sample | Surfactant 2 | Weight of surfactant 2 | Weight of Pluronic L121 |
|---|---|---|---|
| 101 (present invention) | Polyglyceryl dodecyl ether | 0.21% | 2.65% |
| 102 (present invention) | Polyglyceryl distyl phenyl ether | 0.21% | 2.65% |
| 103 (present invention) | Polyglyceryl tristyl phenyl ether | 0.21% | 2.65% |
| 104 (present invention) | Polyglyceryl tribenzyl phenyl ether | 0.21% | 2.65% |
| 105 (comparative example) | Polyoxyethylene octyl phenyl ether (HS210) | 0.21% | 0.53% |
| 106 (comparative example) | None | 0 | 2.65% |

Polyglyceryl dodecyl ether

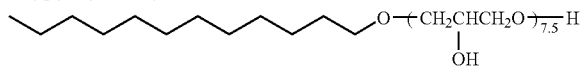

Polyglyceryl distyl phenyl ether

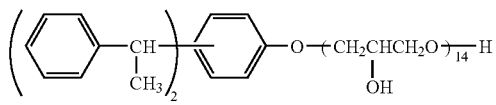

Polyglyceryl tristyl phenyl ether

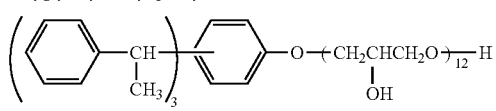

Polyglyceryl tribenzyl phenyl ether

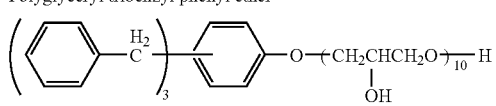

TABLE 2

| Sample | Surfactant 2 | $A_{HDL80}/A_{LDL250}$ |
|---|---|---|
| 101 (present invention) | Polyglyceryl dodecyl ether | 4.58% |
| 102 (present invention) | Polyglyceryl distyl phenyl ether | 5.52% |
| 103 (present invention) | Polyglyceryl tristyl phenyl ether | 4.86% |
| 104 (present invention) | Polyglyceryl tribenzyl phenyl ether | 5.15% |
| 105 (comparative example) | Polyoxyethylene octyl phenyl ether (HS210) | 12.1% |
| 106 (comparative example) | None | 7.2% |

Example 2

Evaluation of Selectivity for Low Density Lipoprotein (LDL) in Mixed Lipoprotein Comparison Between Sample 101 and Sample 103

Reagent 1

| MOPS (pH buffer, pH 7.0) | 50 mM |
|---|---|
| DAOS (manufactured by Dojindo Laboratories) | 1 mM |

(DAOS is a chromogen.)

Reagent 2

| MOPS (pH 7.0) | 50 mM |
|---|---|
| 4-aminoantipyrine | 2.5 mM |
| Pluronic L121 | 2.65% |
| Polyglyceryl dodecyl ether (101) or Polyglyceryl tristyl phenyl ether (103) (surfactant 2) | 0.21% |
| Peroxidase (manufactured by Toyobo Co., Ltd.) | 20 U/ml |
| Cholesterol esterase (lipoprotein lipase, Toyobo) | 1 U/ml |
| Cholesterol oxidase (recombinant *E. coli*, Kikkoman) | 3 U/ml |

The following specimens were used as a specimen:
A specimen obtained by mixing HDL and LDL in such a way that the final concentration of HDL-C is 80 mg/dL HDL-C and that of LDL-C is 150 mg/dL;
A specimen having the LDL-C final concentration of 150 mg/dL 480 µL of reagent 1 was mixed with 160 µL of reagent 2, and the mixture was then incubated at 37° C. for 5 minutes. Five minutes later, 13 µL of the specimen was added to the resultant, and they were then reacted at 37° C. for 5 minutes.

The prepared samples were each measured using spectrophotometer, in terms of the absorbance at 600 nm 5 minutes later, and the results were summarized in Table 3. The term "$(A_{LDL150+HDL80}-A_{LDL150})/A_{LDL150}$" is used herein to indicate an indicator with respect to the selectivity for LDL. The smaller the value, the higher the selectivity for LDL that can be obtained. In case of mixed lipoprotein, higher selectivity for LDL can be obtained when polyglyceryl tristyl phenyl ether (103) is used as surfactant 2.

TABLE 3

| Sample | Surfactant 2 | $A_{LDL150+HDL80} - A_{LDL150})/A_{LDL150}$ |
|---|---|---|
| 101 (present invention) | Polyglyceryl dodecyl ether | 51.3% |
| 103 (present invention) | Polyglyceryl tristyl phenyl ether | 26.2% |

Example 3

Evaluation of Multi-Specimen Correlation

Reagent 1

| MOPS (pH 7.0) | 50 mM |
|---|---|
| DAOS (manufactured by Dojindo Laboratories) | 1 mM |

Reagent 2

| MOPS (pH 7.0) | 50 mM |
|---|---|
| 4-aminoantipyrine | 2.5 mM |
| Pluronic L121 | 4.0% |
| Polyglyceryl tristyl phenyl ether | 0.21% |
| Peroxidase (manufactured by Toyobo Co., Ltd.) | 20 U/ml |
| Cholesterol esterase (lipoprotein lipase, Toyobo) | 4 U/ml |
| Cholesterol oxidase (recombinant *E. coli*, Kikkoman) | 1 U/ml |

Twelve human serums were used as a specimen. 480 µL of reagent 1 was mixed with 160 µL of reagent 2, and the mixture was then incubated at 37° C. for 5 minutes. Subsequently, 13 µL of the specimen was added to the resultant, and they were then reacted at 37° C. for 5 minutes. Using spectrophotometer, the absorbance at 600 nm 5 minutes later, was measured. There was prepared a calibration curve that indicated the relationship between the concentration of the LDL cholesterol of the specimen (which was an LDL-C value obtained by measuring total cholesterol, HDL-C and TG using a commercially available kit, and then calculating it according to the Friedewald formula) and the absorbance at 600 nm. Using the thus prepared calibration curve, the LDL-C of each specimen was obtained, and the correlation of the obtained LDL-C with the LDL value calculated according to the Friedewald formula was then examined. The results are shown in FIG. 1. The correlation coefficient was found to be R=0.9525.

Comparative Example 2

Multi-Specimen Correlation

Figure 2:
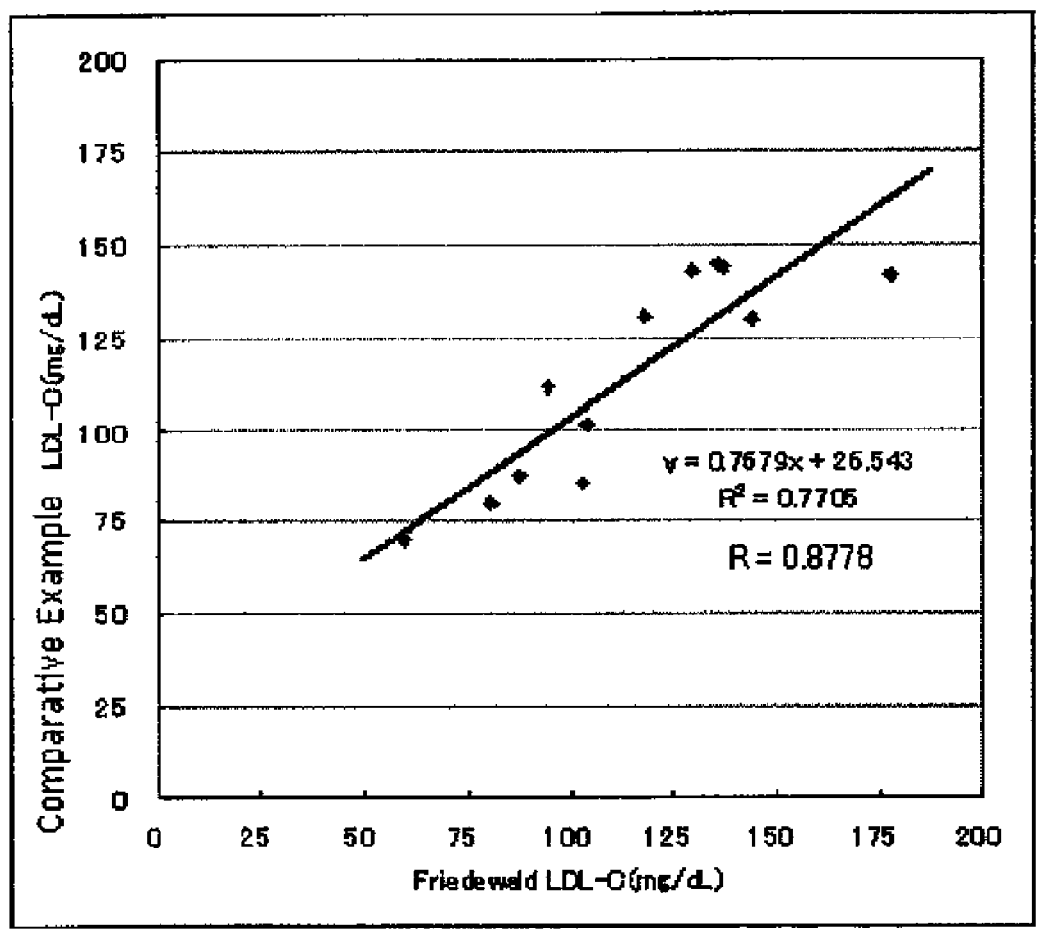
FIG. 2 shows a multi-specimen correlation in the method of the comparative example.

A sample was prepared and evaluated in the same manner as that of Example 2 with the exception that polyglyceryl tristyl phenyl ether was replaced with polyoxyethylene octyl phenyl ether (HS210). Thereafter, the correlation of the obtained LDL-C with the LDL value was then examined. The results are shown in FIG. 2. The correlation coefficient was found to be R=0.8778.

From the results of Example 3 and Comparative Example 2, it is found that the structure of the present invention exhibits an excellent multi-specimen correlation.

Example 4

A Dry Analytical Element for Measuring LDL-C

A gelatin aqueous solution was coated to a gelatin-undercoated polyethylene terephthalate film of 180 µm in thickness which was smooth, colorless and transparent, to a thickness of 14 µm after drying, followed by drying. The, aqueous solutions with the following compositions were coated, followed by drying.

| | |
|---|---|
| 4-aminoantipyrine | 0.32 g/m² |
| TOOS (Dojindo Laboratories) | 0.62 g/m² |
| Peroxidase (Toyobo) | 12.75 kU/m² |

Water was supplied over the above film in a volume of approximately 30 g/m² such that the film became wet. Tricot knitted fabric prepared by knitting (36 gauge) with polyester spun yarn (corresponding to 50 deniers) was laminated thereon via light pressurization, followed by drying. Thereafter, aqueous solutions with the following compositions were coated to the above fabric, followed by drying.

| | |
|---|---|
| MOPS (pH 7.0) | 1.67 g/m² |
| Polyglyceryl tristyl phenyl ether | 5.02 g/m² |
| Pluronic L121 | 39.75 g/m² |
| Cholesterol esterase (lipoprotein lipase, Toyobo) | 0.65 kU/m² |
| Cholesterol oxidase (recombinant *E. coli*, Kikkoman) | 0.13 kU/m² |

Figure 3:
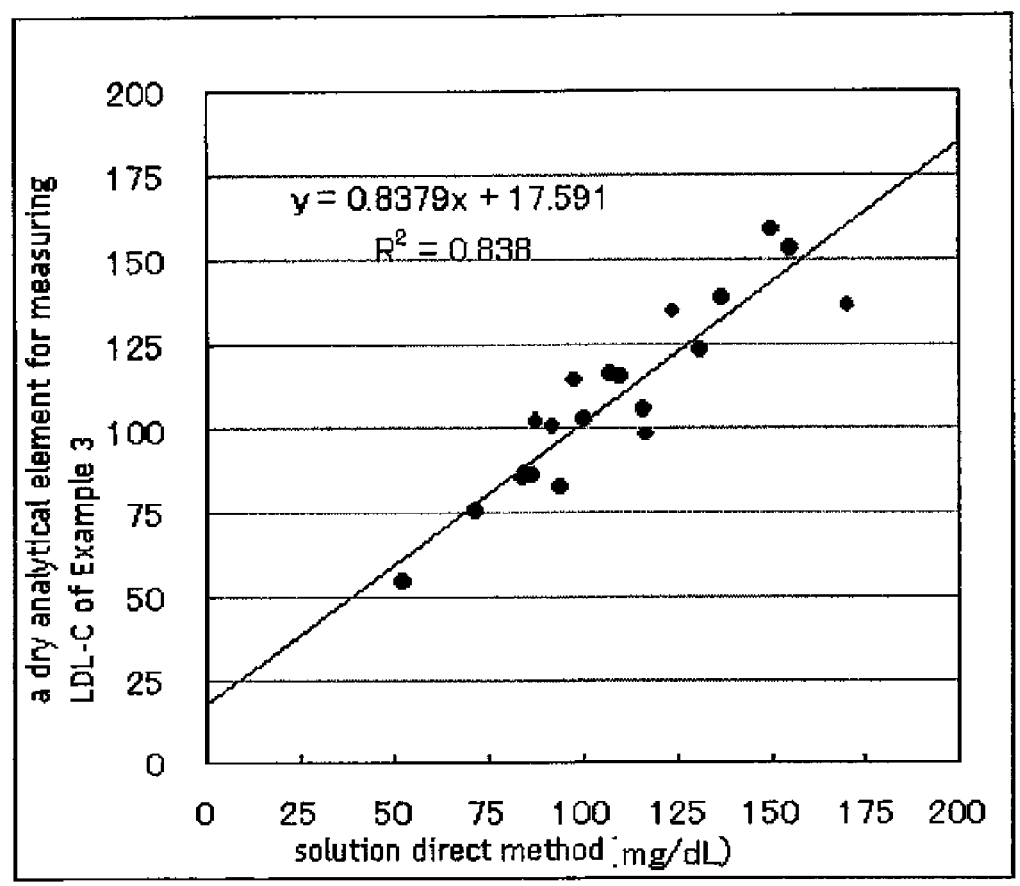
FIG. 3 shows a multi-specimen correlation in the method of the present invention using a dry analytical element for measuring LDL-C.

The multi-specimen correlation was examined in healthy 25 peoples for the method of the present invention and the (solution) direct measurement method. The obtained results are shown in FIG. 3. As shown in FIG. 3, good correlation with the (solution) direct measurement method could be obtained.

The invention claimed is:

1. A method for measuring low density lipoprotein cholesterol (LDL-C) in a body fluid, comprising:
reacting a sample of the body fluid in the presence of:
cholesterol esterase,
cholesterol oxidase,
a polyoxyethylene-polyoxypropylene copolymer, and
a polyglyceryl ether, to form hydrogen peroxide; and
measuring the amount of the hydrogen peroxide, and
comparing the measured amount of hydrogen peroxide to a calibration curve that indicates a relationship between the amount of hydrogen peroxide and LDL-C concentration.

2. The method according to claim 1, wherein the polyglyceryl ether is an aliphatic hydrocarbon polyglyceryl ether or polycyclic polyglyceryl ether.

3. The method according to claim 2, wherein the polycyclic polyglyceryl ether is a compound represented by formula (1):

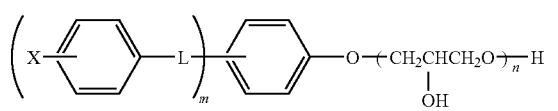

(1)

wherein,
X represents a hydrogen atom, a linear or branched C1-C18 alkyl group, or a halogen atom;
L represents a C1-C5 alkylene group;
m represents an integer of 1 to 5; and
n represents an integer of 3 to 20.

4. The method according to claim 1, wherein measuring the amount of hydrogen peroxide comprises allowing peroxidase to act on the hydrogen peroxide in the presence of a chromogen, so as to carry out a color development reaction.

5. The method according to claim 1, wherein the body fluid is blood, serum, plasma or urine.

6. The method according to claim 1, wherein the cholesterol esterase is lipase.

7. The method according to claim 1, wherein the polyglyceryl ether is polyglyceryl dodecyl ether, polyglyceryl distyl phenyl ether, polyglyceryl tristyl phenyl ether, polyglyceryl tribenzyl phenyl ether, or any combination thereof.

8. A method for measuring low density lipoprotein cholesterol (LDL-C) in a body fluid, comprising:
reacting a sample of the body fluid in the presence of:
cholesterol esterase,
cholesterol dehydrogenase and oxidized coenzyme,
a polyoxyethylene-polyoxypropylene copolymer, and
a polyglyceryl ether, to form reduced coenzyme; and
measuring the amount of reduced coenzyme, and
comparing the measured amount of reduced coenzyme to a calibration curve that indicates a relationship between the amount of reduced coenzyme and LDL-C concentration.

9. The method according to claim 8, wherein the polyglyceryl ether is an aliphatic hydrocarbon polyglyceryl ether or polycyclic polyglyceryl ether.

10. The method according to claim 9, wherein the polycyclic polyglyceryl ether is a compound represented by formula (1):

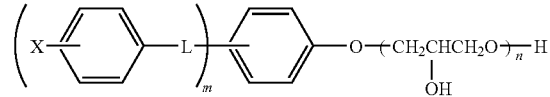

(1)

wherein,
X represents a hydrogen atom, a linear or branched C1-C18 alkyl group, or a halogen atom;
L represents a C1-C5 alkylene group;
m represents an integer of 1 to 5; and
n represents an integer of 3 to 20.

11. The method according to claim 8, wherein the body fluid is blood, serum, plasma or urine.

12. The method according to claim 8, wherein the cholesterol esterase is lipase.

13. The method according to claim 8, wherein the polyglyceryl ether is polyglyceryl dodecyl ether, polyglyceryl distyl phenyl ether, polyglyceryl tristyl phenyl ether, polyglyceryl tribenzyl phenyl ether, or any combination thereof.

* * * * *